United States Patent [19]

Klinger

[11] Patent Number: 5,383,867
[45] Date of Patent: Jan. 24, 1995

[54] UNIVERSAL INCONTINENCE DEVICE

[76] Inventor: Joan Klinger, Box 36, Mount Lemmon, Ariz. 85619

[21] Appl. No.: 65,892

[22] Filed: May 25, 1993

[51] Int. Cl.6 .............................................. A61F 13/15
[52] U.S. Cl. .................................. 604/385.1; 604/358
[58] Field of Search ............... 604/352, 346, 349, 358, 604/351, 353, 385.1; 2/402–405

[56] References Cited

U.S. PATENT DOCUMENTS

| | | | |
|---|---|---|---|
| 4,197,849 | 4/1980 | Bostick | 604/352 |
| 4,326,302 | 4/1982 | Lowe et al. | 2/405 |
| 4,944,733 | 7/1990 | Casale | 2/405 |
| 5,204,997 | 4/1993 | Suzuki et al. | 2/403 |
| 5,207,663 | 5/1993 | McQueen | 604/385.1 |

Primary Examiner—Jerome L. Kruter
Attorney, Agent, or Firm—Breneman & Georges

[57] ABSTRACT

A disposable absorbent universal incontinence device having a front and a back and one or more layers of absorbent material and an outer layer of plastic or waterproof material is provided having in the front a slit or a semi perforated opening extending through one or more absorbent layers to the inside of the garment through the outer layer of plastic or waterproof material of the garment to provide an access opening to allow normal urination by an incontinent male. The slit or semi perforated opening is covered by a flap like member detachably secured around the perimeter or a portion of the perimeter to the outer layer of plastic or waterproof material of the garment. The detachable securement allows the flap to be opened from the top, bottom or sides to provide access from any desired location once the flap is partially removed and the slot or perforated opening is separated to provide access. The universal incontinence device is designed to accommodate both males and females by allowing any fluids that pass through the slit or semi perforated opening to be captured in the center section and the inside surface of the flap closure and prevent any migration of fluids by utilizing a seal provided around the perimeter of the flap-like closure.

20 Claims, 5 Drawing Sheets

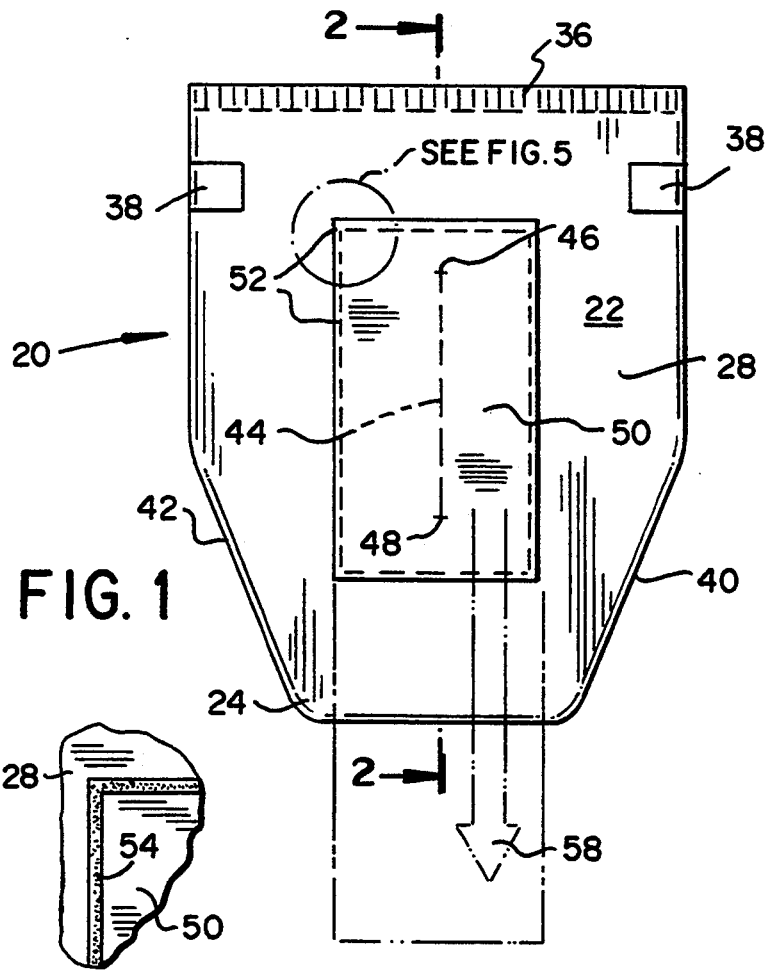
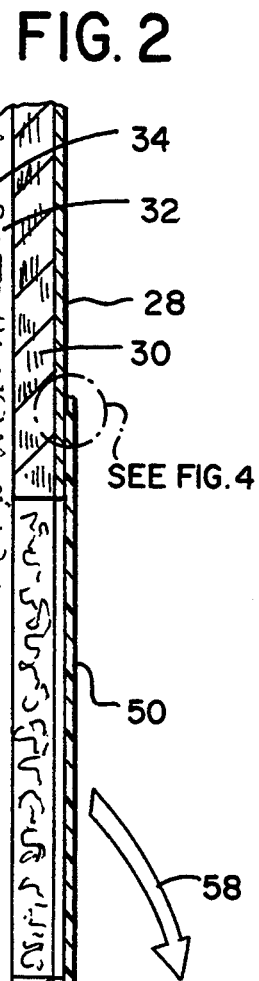
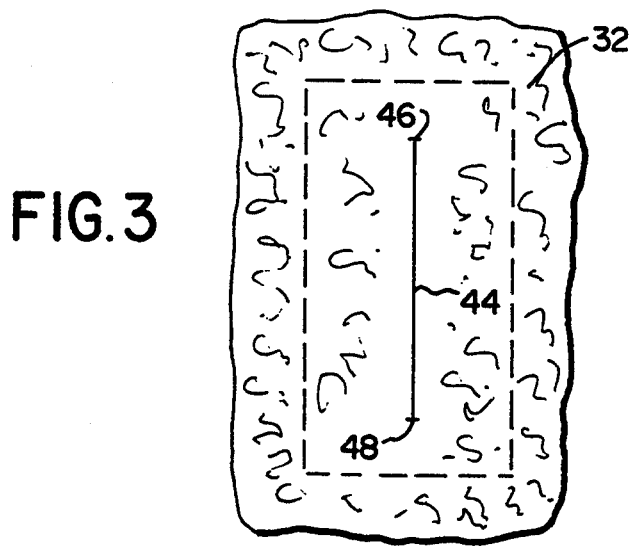
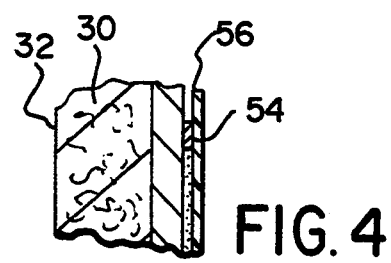

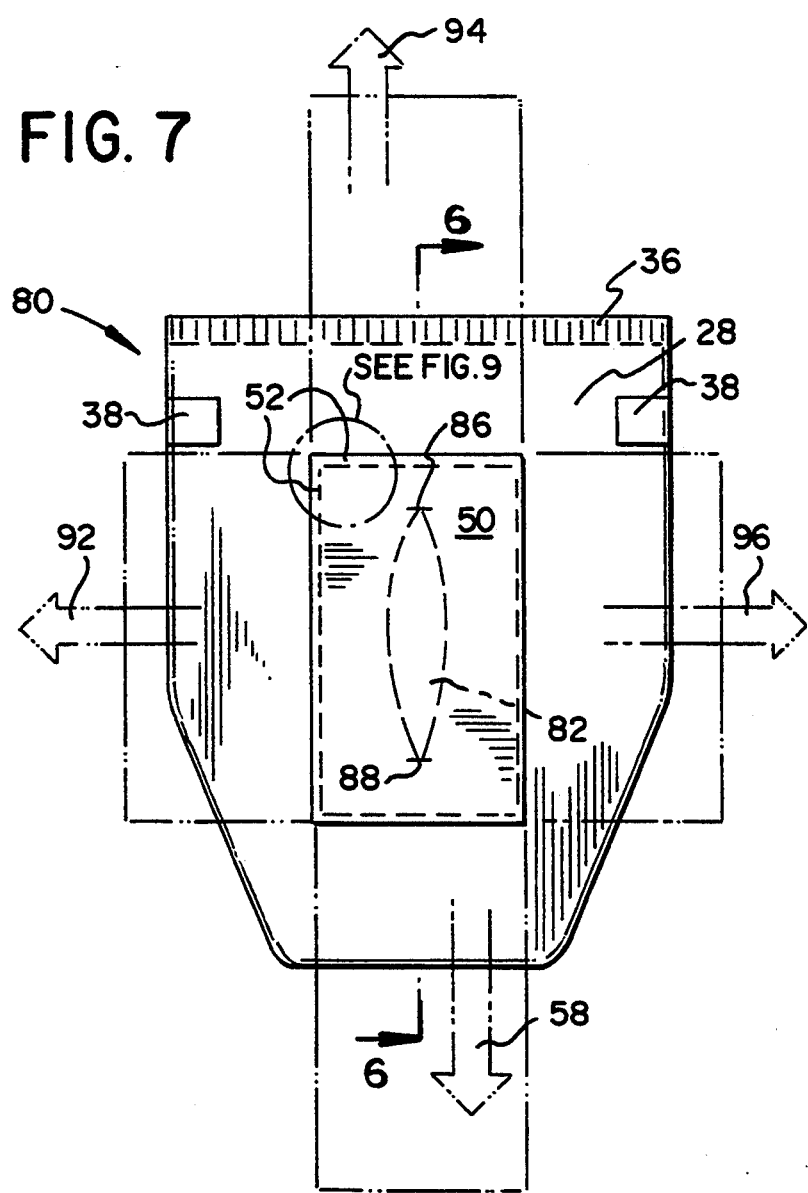
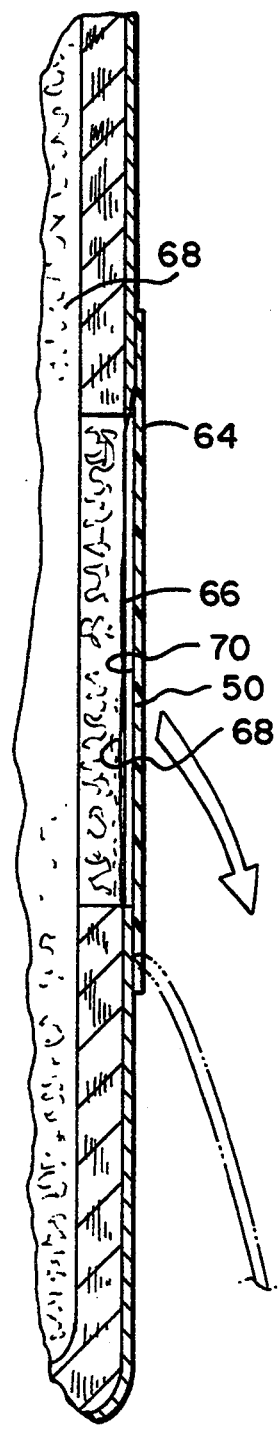
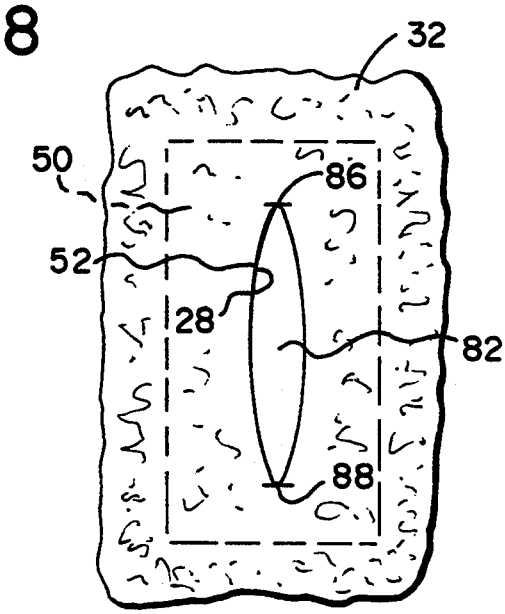

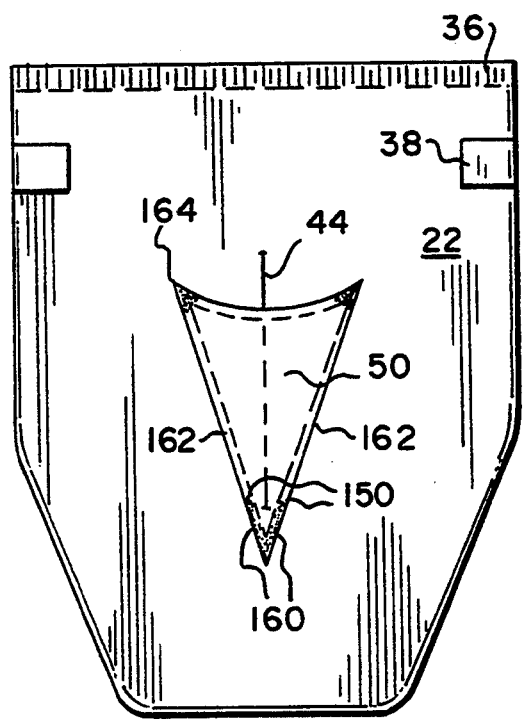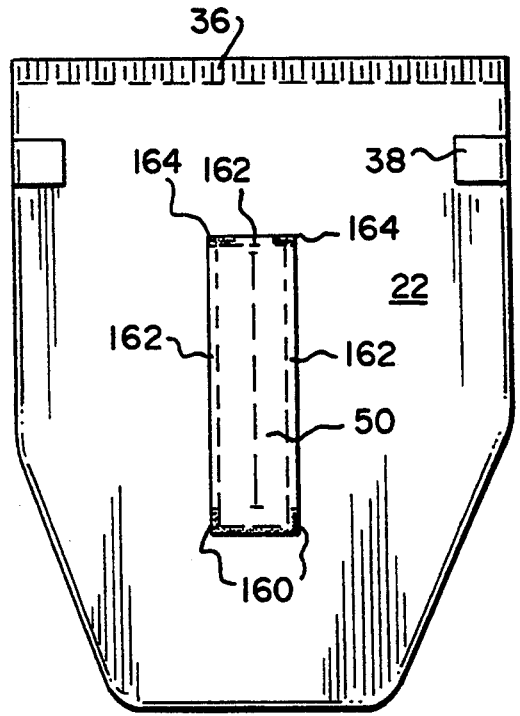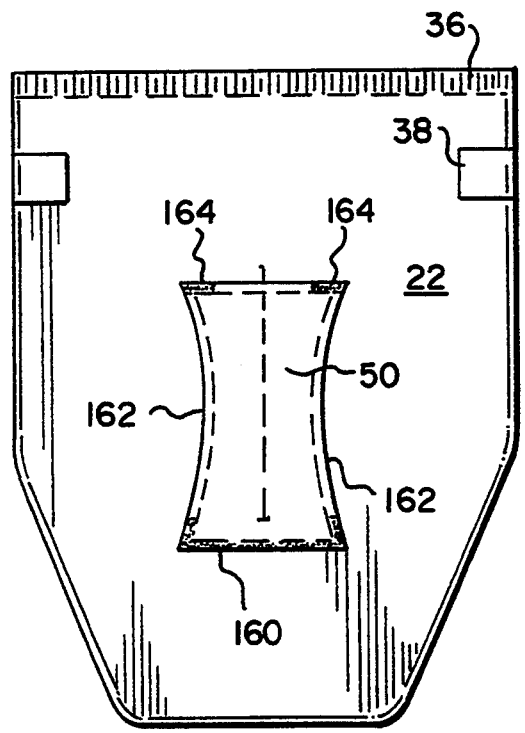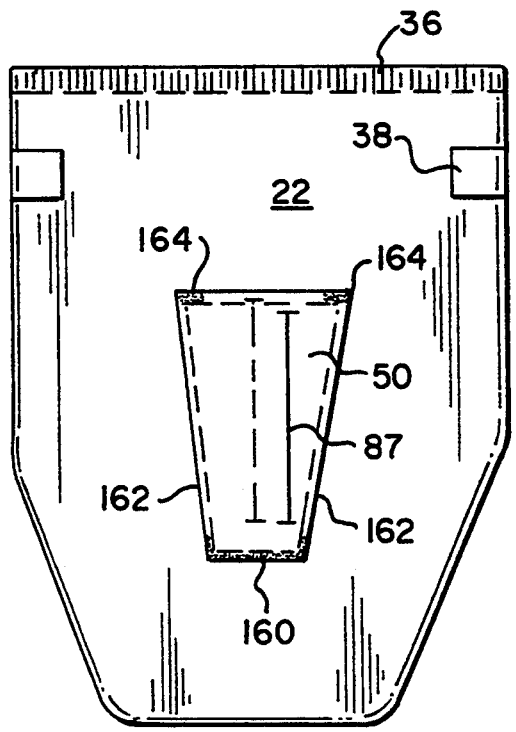

UNIVERSAL INCONTINENCE DEVICE

BACKGROUND OF THE INVENTION

1. Field Of The Invention

The invention pertains to a universal incontinence device suited for wear by either males or females and which at the same time provides all the advantages for access to the male organ for normal urination. Normal urination for the male is provided by the modification of a disposable absorbent incontinence garment by the utilization of a slit or semi perforated opening extending through the layers of the disposable incontinence garment which slit is covered by a flap closure sealed to the outer surface of the disposable incontinence garment. More particularly the invention pertains to the utilization of a flap-like closure attached to the plastic or waterproof front surface of a disposable absorbent garment in combination with a slit or semi perforated opening.

In the preferred application of the invention the flap-like closure is sealed around all or part of its perimeter to the plastic or waterproof outside surface of the disposable incontinence device so that the flap-like closure can be opened from the bottom, top or sides to provide access to the perforated slit or semi perforated opening in the front side of the garment. The flap-like closure also preferably includes an outside surface of plastic or other waterproof material and an inside surface containing an absorbent material for absorbing any water or moisture coming through the semi perforated opening or slit of the disposable universal incontinence device. The flap and slit or semi perforated opening combination may also include means for spacing the flap from the slit to provide aeration of the interior of the garment without allowing body fluids inside the garment from exiting the novel universal incontinence device.

The universal disposable incontinence device may also include indicator means in the flap closure between the outside surface of plastic and the absorbent material for detecting moisture migrating through the slit or semi perforated opening in the front of the incontinence device to provide visual indication for both male and females of the necessity to change the universal incontinence device of the invention. The flap closure and slit or semi perforated opening combination of the invention serve multiple functions by not only providing an access opening for the lightly incontinent male or semi mobile male but also may be used as a means for providing a visual indication at the front of the garment of the necessity to change a wet garment in the case of a bedridden male or female incontinent patient.

The flap-like closure further may include a tacky self-sealing perimeter for assisting in the closure in the universal incontinence device after it has been used by the male for normal urination. The tacky self sealing perimeter may be used alone or in combination with the seal around all or part of the perimeter of the flap like closure. In the preferred embodiment both a heat seal to seal the flap to the plastic outer surface and a tacky seal for repeatable sealing of the flap closure can be employed.

2. Description Of The Prior Art

The prior art includes a number of different types of diapers and undergarments for use by incontinent adults who may or may not be bedridden. The available devices come in a wide variety of formats including light pads or shields to be worn with undergarments to moderate devices which include a front and a back connected by a body fluid collecting center section which may be attached utilizing waist or hip straps for holding the garment on to a maximum security device which generally is in the form of a complete diaper or brief which is held together with side straps or tabs much in the format as illustrated in Strickland, et al. U.S. Pat. No. 4,253,461.

The problems with the known and available prior art devices stem not only from the psychologically debilitating effect of the garment but also from the environmental considerations resulting from the disposal of the vast variety and array of different types of incontinence devices. This environmental problem is further compounded by the fact that such disposable devices are changed and discarded more often than necessary since urination particularly by the male requires either total removal of the incontinence device or urination in the incontinence device which yields the same net effect, namely discarding the diaper in order to have it replaced by a fresh diaper or incontinence device.

The failure of the known prior art to provide for a means for access to the male organ by the lightly incontinent male or the partially bedridden adult has increased the disposal problems since many times garments are discarded due to the inability of the lightly incontinent male to obtain access for urination and the problems encountered in attempting to reaffix a strapped or tapped incontinence device after it has been removed. Generally it is so cumbersome to remove and replace a prior art incontinence device that disposal is the practical solution causing further problems to the environment. The invention in contrast to the prior art provides flexibility and psychological security to the incontinent male by allowing the lightly incontinent male or slightly bedridden incontinent male to utilize the universal disposable incontinent device of the invention as a longer lasting but ultimately disposable undergarment.

The provision for access allows the lightly incontinent or semi bedridden male to utilize the universal incontinence device of the invention more as a semi disposable pair of briefs which can be worn until disposal becomes necessary due to its becoming soiled with body fluids. The psychological advantages to patients are achieved by providing the option for normal urination while at the same time providing the security of an incontinence device which can be comfortably used by both males and females should assist in the reduction in the volume of discarded incontinence devices. These advantages are combined with more comfort in wearing the novel incontinence device of the invention by providing aeration to the interior of the garment by a means for spacing the flap from the slit or semi perforated opening. This in combination with the advantages of providing either a slit or a semi perforated opening in the undergarment covered by a flap closure having an absorbent back side and a waterproof front side allows the addition of absorbent indicators to provide the visual confirmation of moisture to provide additional advantages to the flap like closure for the bedridden incontinent patents.

The known prior art devices such as Strickland, et al. U.S. Pat. No. 4,253,461 provides for absorbent briefs or disposable incontinence devices to be held to the wearer's body by means of tabs for connecting the front portion and back portion. Strickland, et al. U.S. Pat. No. 4,253,461 does not provide access for the male to allow normal urination. Strickland, et al. U.S. Pat. No. 4,253,461 like the other prior art requires either complete removal of the brief in order to provide access to the male organ and which like the other prior art generally requires disposal of the brief after removal due to the difficulties in replacing and repositioning the article to the wearer's body.

Other devices such as Thorner U.S. Pat. No. 4,644,945 provides for a cuff-like pad or pocket for use with loose fitting mens' garments to collect body liquids for men. This device is not universal in that while providing access for the male the garment cannot be worn by both the male and the female. Sivilich U.S. Pat. No. 4,589,877 provides an undergarment shield for lightly incontinent males having two pads slidable in relation to one another and a longitudinal slit placed in a panel connecting the two pads. Sivilich U.S. Pat. No. 4,589,877 is not an incontinence device but merely is a pad for males and therefore is not a universal incontinence device which may be used by both males and females. However, more importantly Sivilich U.S. Pat. No. 4,589,877 imparts considerable bulk to the garment as a result of its arrangement utilizing two sliding pads or panels in order to provide access. The addition of pads or panels and additional bulk is not desired in an incontinence garment since the bulk makes access more difficult and results in greater bulk in disposing of the pads to the environment.

The prior art as a result does not provide a universal incontinence device that is both user friendly and environmentally friendly by providing a more normal access to the lightly incontinent or partially bedridden male while at the same time suitable for use for the female and for reducing the bulk of discarded incontinence garments in the environment. It is therefore an object of the invention to provide a universal incontinence garment which may be worn by either men or women and which may be readily opened and closed to provide access to the male which is relatively simple to manufacture and which reduces the bulk of disposed garments to the environment.

It is a further object of the invention to provide a garment which may be used for either the mildly incontinent patient or the bedridden patient which does not have to be removed by the male to provide access for normal urination and which provides comfort to the male or female wearer by providing aeration to the interior of the garment while preventing moisture from migrating out of the garment.

It is a further object of the invention to provide an indication of moisture by allowing the migration of body fluids through the absorbent layers and through a slit or semi perforated opening in the plastic or waterproof covering of a garment to access a color indicator in the outside flap to provide a visual indication of the need to change the garment in either the male or female incontinent bedridden patient.

It is also a further object of the invention to provide a universal device that may be used by both males and females and not have to be removed and discarded until removal and discarding is necessary as a result of the garment becoming soiled with body waste fluids.

SUMMARY OF THE INVENTION

The disadvantages and limitations of prior art disposable incontinence devices and disposable diapers are obviated by providing a universal incontinence device which may be worn by either males or females and which provides access for normal male urination without the necessity of removing the entire incontinence device from the body. The universal incontinence device in providing access for normal urination by males assists in the protection of the environment since removal is not necessary for normal urination and the novel universal incontinence device can be worn until such time as it is soiled by bodily fluids.

The novel universal incontinence device can be utilized by the mildly incontinent patient as well as bedridden adults whether they be male or female. The advantages of the invention are provided by the utilization of a single universal incontinence device thereby reducing the variety of incontinent devices and reducing the amount of packaging and number of products since the novel universal incontinence device of the invention can be utilized for the light, moderate, heavy and complete needs heretofore generally accommodated by three or four different varieties of incontinence devices of the prior art.

The advantages of the novel universal incontinence device are achieved by utilizing a slit or semi perforated opening in combination with a flap in a garment having a front and a back and a fluid receiving section disposed therebetween. The universal incontinence device includes an inner body contacting layer and one or more layers of the absorbent material and an outer waterproof layer. The front side of the garment includes a semi perforated area or slit extending through the inner layer and one or more absorbent layers and the outer plastic or waterproof layer to provide a means for access for the male organ to provide for normal urination. A flap like closure is provided to cover the semi perforated area or slit which flap is preferably sealed around all or a portion of the perimeter of the flap to the plastic or waterproof outer layer of the novel garment.

The flap is preferably constructed of two or more layers which include an outside layer made of plastic or other waterproof material and an inside layer made of absorbent materials to capture any fluids emanating from the slit or semi perforated opening to the flap. The flap may optionally include an indicator layer of dye disposed between the outside plastic or waterproof layer so that any body fluids migrating through the semi perforated opening or slit can contact an indicator dye on the backside of a transparent or translucent flap to visually indicate the need to change the novel universal incontinence device. The flap layer may optionally include an absorbent inner liner where a slit is used so that moisture may be directed away from the slit and into the absorbent inner liner of the flap so that moisture is directed away from the body and any dyes in the outer layer of the flap do not migrate back to the body of the wearer thereby resulting in skin irritation or dyes being present on the wearer or patient's body.

The flap like closure is preferably detachably sealed on all four sides around its perimeter but may be sealed on less than four sides particularly where the top of the flap and the upper perimeter of the novel universal incontinence device provides a means for aeration of the interior of the garment while preventing fluids from escaping the garment since fluids migrate toward the bottom or lower portion of the front side and down into the fluid capturing intermediate section of the incontinence device. In this manner areation is provided without the possibility of undesirable leakage. The flap may also be opened from the top and pulled down to provide access for the mildly incontinent or slightly bedridden patient while at the same time allowing the device to be utilized by the female and provide the same degree of protection as prior art devices while providing the additional advantages of aeration which make the universal incontinence device more comfortable to the patient or wearer. Unlike the prior art incontinence devices which become uncomfortable due to body heat and the sealing of the device around the waist and legs of the patient the invention allows the access of air into the interior of the garment by allowing the garment to breathe. The prior art has provided a greater degree of security for body fluids captured in the absorbent layers in the center section and bottom portions of the front and back sides of the incontinence device at the expense of comfort and the lack of the access of air into the interior of the garment. The provision for aeration by allowing the top end of the flap to be slightly opened away from the slit and body of the garment provides the advantages of allowing air flow into the interior of the garment while at the same time not interfering with the ability of the novel universal incontinence device to capture and hold body fluids in the absorbent layers since body fluids migrate down from the front section to the center fluid capturing section of the incontinence device.

The flap for sealing the semi perforated opening or slit may include a heat seal, a tacky film seal or a combination thereof for sealing the perimeter of the flap to the plastic or waterproof section of the novel incontinence device. Generally a combination of seals may be used such as a heat seal at the lower end and a tacky film sealant at the top end which can be repeatedly opened and closed up against the plastic or waterproof outer covering of the novel incontinence device. A combination of a heat seal and tacky mechanical sealing may also be arranged so that when the heat sealed portion is opened a tab or strip may be removed to expose a tacky section which thereafter operates as a repeated sealing mechanism when used by the male.

The novel universal incontinence device may be used by either the male or the female and provide for normal urination by the male and provide a device that is much more akin to the normal briefs worn by the male while at the same time providing the same degree of security as found in incontinence devices which do not include the provision for normal male urination. In addition the novel universal incontinence device of the invention provides psychological advantages to the incontinent male in providing a brief more like the briefs ordinarily used by the male while at the same time providing the same degree of security as other incontinence devices thereby reducing the amount of discarded devices which once removed from the body by opening the side tabs are difficult to replace to the wearer's body. The novel universal incontinence device of the invention also reduces the number and variety of devices utilized in the prior art which have not provided for normal male urination. The prior art devices have required removal from the wearer to provide for urination followed by discarding after removing the prior art incontinent devices.

The novel universal incontinence device of the invention further provides advantages in allowing indicators to be utilized to indicate whether the novel incontinent device has been soiled by utilizing dyes which are kept away from the body by utilizing the flap which may include optional absorbent layers and indicator dyes to indicate the presence of moisture. The flap may also be modified to provide for aeration and a more comfortable garment by providing a passage at the top of the flap to communicate with the semi perforated area or slit in the incontinence device to provide for aeration. These and other advantages of the invention will become apparent from the following description of the drawings and preferred embodiment.

DESCRIPTION OF THE DRAWINGS

Other advantages of the invention will become apparent to those skilled in the art from the following detailed description of the preferred embodiment in conjunction with the drawings in which:

FIG. 1 is a front elevational view of a novel universal incontinence device constructed in accordance with the invention;

FIG. 2 is a section view taken along the lines 2—2 of FIG. 1;

FIG. 3 is a plan view taken from the inside of a portion of the novel incontinence device illustrating the arrangement between the perforated opening and closure flap;

FIG. 4 is an enlarged sectional view of the referenced portion of FIG. 2;

FIG. 5 is an enlarged sectional view of the referenced portion of FIG. 1;

FIG. 6 is a side elevational view of a section of an alternative embodiment of the closure flap;

FIG. 7 is a front elevational view of a modification of the novel universal incontinence device illustrating multiple possible optional openings for the closure flap;

FIG. 8 is a plan view from the inside of a portion of the modified universal incontinence device of FIG. 7;

FIGS. 17-20 are front elevational views of further embodiments of flap and slit or semi perforated openings for the novel incontinence device of the invention.

DETAILED DESCRIPTION OF THE INVENTION

Figure 9:
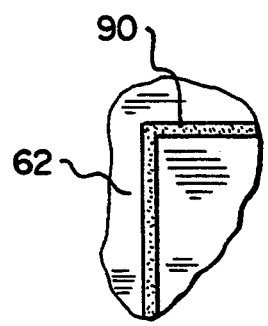
FIG. 9 is an enlarged section of a portion of FIG. 7.

For the purposes of the description of this invention the phrase "universal incontinence device" refers to a disposable absorbent diaper or incontinence device designed to be worn both by the male and female and which provides access for the male to the male organ for ordinary urination. The traditional ordinary urination contemplated includes access through the front of the universal incontinence device by a slit or semi perforated opening which is sealed by a flap and maintained in a closed position for use by females. The flap and slit or semi perforated opening may be opened as needed or desired by the slightly incontinent or partially bedridden male patient. The sealing contemplated by the invention includes both a thermoseal for thermally sealing around a substantial portion or the entire perimeter of the interface between the flap and the waterproof or plastic outer layer of adult diapers or absorbent briefs.

Referring now to FIG. 1 an absorbent diaper or brief 20 is illustrated having a front section 22, a center section 24 and a rear section 26 (not shown) having a configuration substantially similar to the front section but without a slit or perforation. The front section 22 as well as the entire garment includes an outside cover 28 which is made of plastic or other waterproof material which covers a corresponding layer of absorbent material 30. Absorbent material 30 may be one or more layers made of cotton or other moisture absorbent material including powders or gels which absorb and trap moisture in the absorbent material 30. A generally moisture pervious backsheet 32 can be provided to transport moisture away from the wearer's skin 34 and into the absorbent material 30.

The universal incontinence device 20 includes an elasticized waist band 36 or other means for constricting the incontinence device around the waist of a wearer such as a tie or drawstring alone or in combination with the elasticized waist band 36. Tabs 38 may be utilized to assist in attaching the novel universal incontinence device to the wearer alone or in conjunction with the elasticized waist band 36 or draw cords or straps (not shown) may be utilized alone or in combination with an elasticized waist band or tabs to secure the upper part of the novel universal incontinence device to the waist of the wearer and provide a degree of variation in waist sizes. The leg opening 40 and 42 may similarly include constricting means for assisting in the closure of the novel universal incontinence device around the legs of the wearer.

As will be recognized by those skilled in the art the close fit provided by the constriction of the leg opening 40 and 42 as well as the constriction provided by elasticized waist band 36 provide greater degrees in security against leakage and assist in fit but also provide for less aeration which results in sweating and moisture becoming trapped due to the water proof nature of the plastic outer covering. This problem of security versus comfort in view of aeration requirements will be discussed hereinafter in greater detail with respect to various modifications in accordance with the preferred embodiment of the invention.

The novel universal incontinence device includes a semi perforated opening or a slit 44 which may extend through outside cover 28 and through absorbent material 30 and through the generally moisture pervious liner or backsheet 32 to provide access to the male organ for normal urination. Slit 44 may be either a uniform slit through all the layers or be a slit which extends only through layers 32 and 30 and includes a partially perforated opening in outside cover 28 so that it may later be pulled apart to provide access for the male. Slit 44 may optionally also include perforated ends 46 and 48 which prevent undue tearing of the garment and in particular outside cover 28 which might otherwise impair the waterproof integrity of outer cover 28.

Referring now to FIGS. 1-5 slit 44 which may be only partially perforated through the layers or actually include a slot shaped opening such as illustrated in FIG. 8 is covered by a flap or closure 50 which is also constructed of plastic or made of a waterproof material. Flap 50 is secured at its outer perimeter 52 to outside cover 28. Flap 50 may be secured by means of a heat seal 54 and include an overlapping tab 56 to provide access to the male wearer of the garment without having to remove the garment by removing tabs 38 or pulling the garment down or otherwise repositioning the garment with respect to the body of the wearer. In this manner flap 50 may be removed by pulling on overlapping tab 56 to separate heat seal 54 from outside cover 28 to move the entire flap 50 from its closed position in FIG. 1 to its opened position as illustrated by arrow 58 (FIG. 2) to provide access to the male organ for normal urination.

Figure 10:
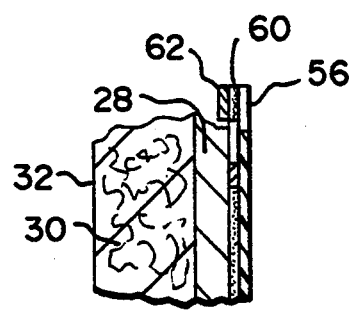
FIG. 10 is a side elevational view of FIG. 9.

Once the heat seal 54 is broken flap 50 may be replaced to its closed position and held in place by trousers or other outer garments. In the preferred application of the invention a second seal 60 (FIG. 10) is provided on the underside of overlapping tab 56 to assist in maintaining flap 50 in the closed position once the heat seal 54 has been broken. Second seal 60 may include a tacky sealant which may include a backing strip 62 to prevent deterioration of seal 60 prior to use.

Alternatively heat seal 54 may include other sealing materials such as rubberized compounds or a sticking backing or tacky backing for providing a reusable seal as opposed to a heat seal to outside cover 28. In the preferred embodiment of the invention a combination of heat seal and tacky seal is used with the heat seal sealing the bottom of the flap against the outer cover 28 and a tacky second seal 60 disposed at the top of flap 50 so that a tacky or sticky surface remains available around the upper perimeter of flap 50 so that it may be opened and closed repeatedly without destroying the integrity of the seal. This is particularly advantageously applied where flap 50 includes multiple layers where the outside layer 64 of flap 50 is made of plastic and an inside layer includes an absorbent layer 66 (FIG. 6). Absorbent layer 66 of flap 50 in FIG. 6 may also include cotton or various gels or absorbent materials to trap moisture.

Flap 50 may also have an optional liner layer 68 which like the backsheet 32 assists in directing moisture deposited on flap 50 through slit 44 into absorbent layer 66. Flap 50 may also include an optional layer 70 made up of an indicator dye on the backside of flap 50 to indicate the presence of moisture on flap 50 to visually indicate the necessity of changing the novel universal incontinence device of the invention. Layer 70 may be any type of indicator dye which indicates the presence of moisture or urine by detecting either changes in pH or moisture by providing a color change which then may be observed through flap 50.

In applications employing an indicator dye it is desirable for flap 50 to be clear or semi transparent so that changes in color can be observed through the plastic or waterproof material of flap 50. A No. 7700 FD&C Red #40 dye as may be obtained from Warner Jenkins of St. Louis, Mo. may be used as well as a variety of other indicators that may be applied to strips or on plastic films or directly onto the back side of the plastic or waterproof material of flap 50. The utilization of a dye allows the novel universal incontinence device to be removed where a visual indication of moisture is present without having the severely incontinent or bedridden patient being checked manually for moisture by the attendant.

Referring now to FIGS. 7, 8 and 9 a further embodiment of the novel universal incontinence device is illustrated in which similar numbers have been utilized for similar structure. The major difference between the novel universal incontinence device 80 of FIGS. 7, 8 and 9 is in the provision of an oval opening 82 in place of slit 44. Oval opening 82 provides greater access to the male organ for urination and in this embodiment flap 50 includes multiple layers of absorbent padding as illustrated in FIG. 6 so that when universal incontinence device 80 is worn by a female moisture not caught or captured in center section 24 is absorbed by absorbent layer 66 of flap 50. Oval opening 82 may further include stress cuts 86 and 88 to prevent unwarranted tearing or ripping of outside cover 28 which could destroy the waterproof integrity of the garment by allowing any rip or tear to extend outside the perimeter 52 of flap 50.

Oval shaped opening 82 as well as slit 44 may include the heat sealing of outside cover 28 to backsheet 32 around the periphery of opening 82 or slit 44 to prevent undesired entanglement with the absorbent materials or powders or gels that may be present or utilized in the absorbent material 30. The use of an oval shaped opening may be utilized in combination with an offset slit 87 (FIG. 20) in flap 50 to provide access through flap 50 and through slit 44 or oval shaped opening 82 to the interior of the novel universal incontinence device.

The other major difference between universal incontinence device 20 and 80 is the perimeter 52 of flap 50 which is sealed against outside cover 28 by the utilization of a tacky or sticky mass 90 (FIG. 9) that is substantially non degraded by water but which provides for good adhesion between the plastic of outside cover 28 and the plastic edge of flap 50. Tacky layer 90 is designed to seal the entire perimeter 52 of flap 50 so that flap 50 may be opened and resealed in the direction of not only arrow 58 but also arrow 92, arrow 94 and arrow 96. Tacky layer 90 may either be provided on flap 50 or on layer 28 or a combination thereof to provide a seal around the perimeter of flap 50.

Figure 11:
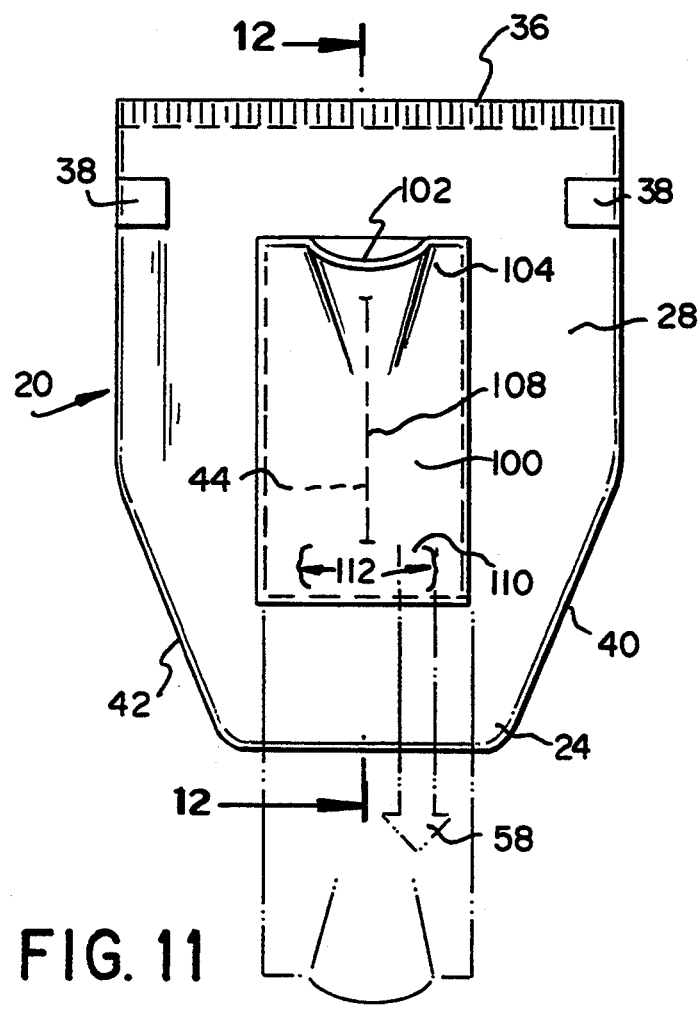
FIG. 11 is a further alternative embodiment of the novel universal incontinence device of the invention.
Figure 12:
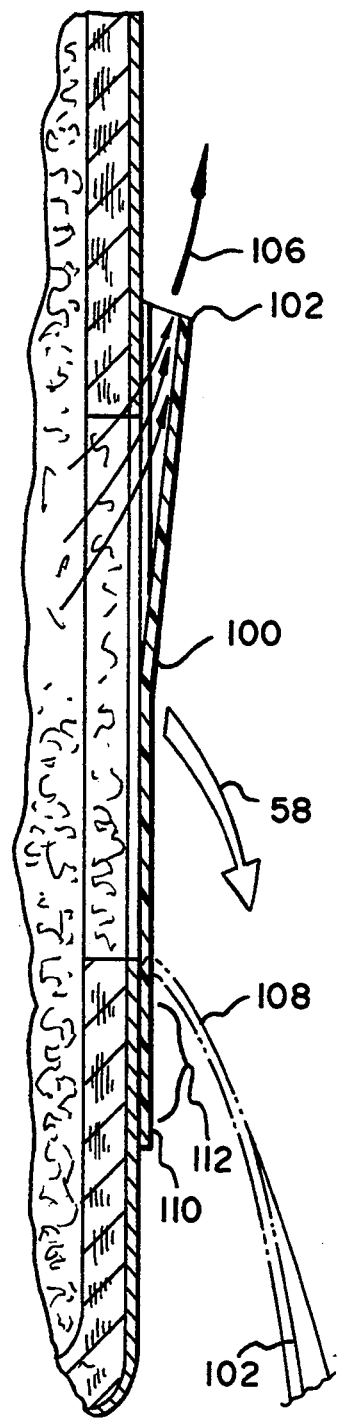
FIG. 12 is a sectional view of a portion of the incontinence device taken along the line 12—12 of FIG. 11.

The novel universal incontinence device may further be modified as illustrated in FIG. 11 and FIG. 12 to provide an opening for aeration into the interior of the brief which may communicate with either slit 44 or opening 82 to provide aeration and additional comfort to the wearer. The novel universal incontinence device 20 in FIG. 11 includes a modified flap 100 for covering a slit 44 or opening 82 to provide aeration to the novel universal incontinence device without in any way deleteriously affecting its performance in preventing the escape of body fluids. The body of the novel universal incontinence device is the same as previously described with respect to FIG. 1 except that flap 100 includes a funnel shaped opening 102 at the top end which prevents the upper end 104 of flap 100 from closing the center section of upper end 104 against outside cover 28.

Funnel shaped opening 102 allows the aeration of the body through slit 44 or an opening 82 to provide the ingress and egress and circulation of air as indicated by arrow 106. Funnel shaped opening 102 also provides the additional advantage of assisting elderly and invalid patients in opening and closing flap 100. Funnel shaped opening 102 can taper the entire length of slit 44 or opening 82 but in the preferred application tapers only about 50 percent of the length of the opening particularly in applications where flap 100 does not include an absorbent inner layer to assist in the capture of moisture in the absorbent material 30.

The placement of the funnel shaped opening 102 at or near the top of the front section 22 of the novel universal incontinence device 20 assures that body fluids will not leak or drip from the garment since it is disposed high above the center of gravity for the normal flow of body fluids since fluids flow down to the center section 24 and down to the bottom portion 110 of flap 100. The flap 100 is attached to cover 28 so that any fluid passing through slit 44 or opening 82 is captured in bottom portion 110 between flap 100 and cover 28 in the area 112 to prevent the accidental discharge of fluids. Flap 100 may also include an absorbent inner layer which may extend the entire length of flap 100 or only from the point 108 at which the funnel shaped opening terminates. Flap 108 may further include dyes or indicators for moisture so that a soiling of the novel universal incontinence device of the invention may be determined visually. In all applications of visual indication the dyes are carried in the flap portion 50 or 100 and thus away from the skin and body of the wearer so that a visual indication of wetness does not interfere or contact with the skin of the wearer.

Figure 13:
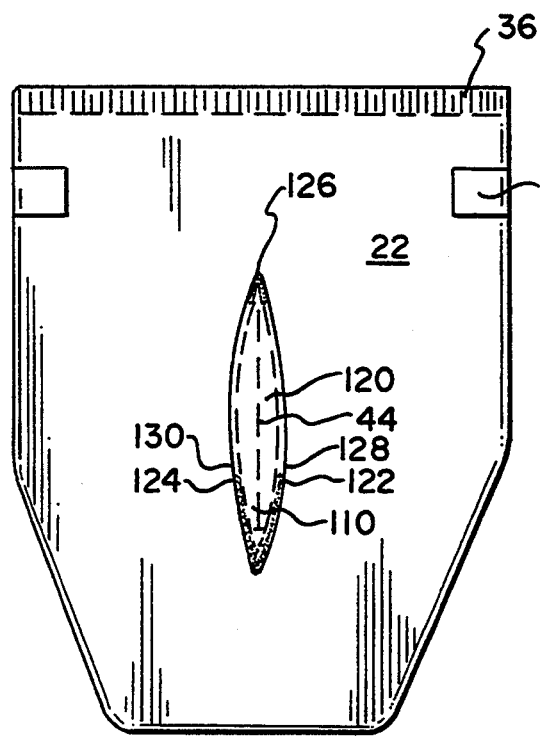
FIG. 13 is a front elevational view of a further embodiment of the novel incontinence device of the invention.
Figure 14:
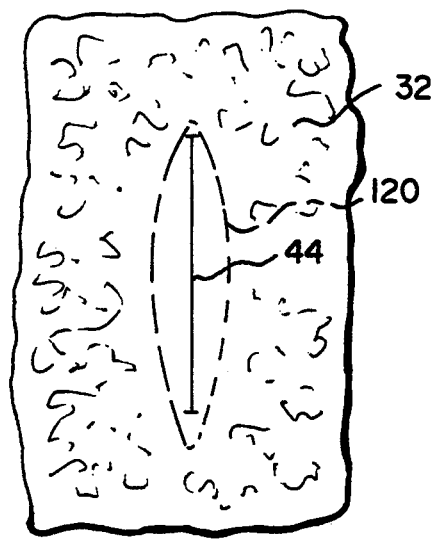
FIG. 14 is a plan view from the inside of a portion of the novel incontinence device of FIG. 13.

Referring now to FIG. 13 and 14 an alternative flap 120 of an elliptical configuration is illustrated in combination with a slit 44. Flap 120 is heat sealed to provide a permanent seal from area 122 to area 124 to prevent any accumulation of body fluids at area 110 from escaping from the garment. A spot heat seal 126 is provided at the top of flap 120 which may be opened to provide access. Once access is provided a tacky seal extends from point 128 to point 130 around flap 120 to provide for repeated opening and closing of flap 120. As will be recognized by those skilled in the art only a portion of the perimeter of the flap needs to be sealed to the plastic cover of the brief. Typically 60 to 100 percent of the perimeter of the flap is sealed of the plastic layer of the brief. However depending upon the shape of the flap as little as 10 percent of the perimeter of the flap may be sealed to the plastic outer layer of the brief, particularly where a combination of permanent and reclosable seal such as tongue and groove or tacky seals are employed.

Figure 15:
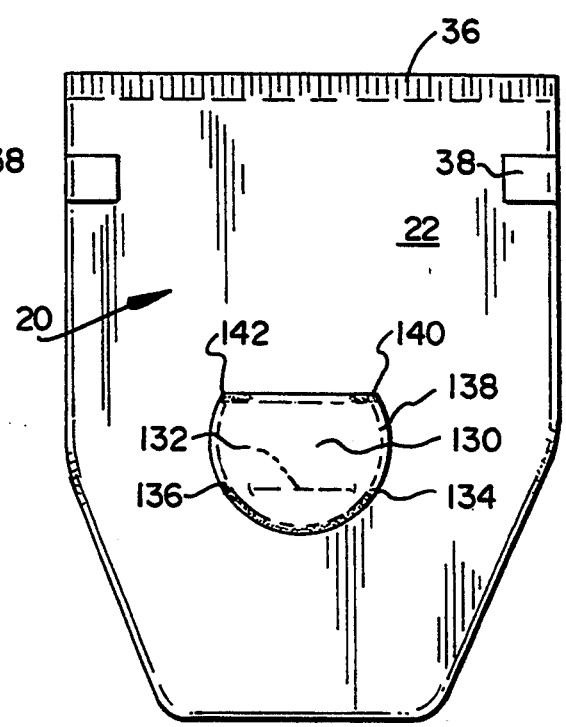
FIG. 15 is a front elevational view of a further embodiment of the novel incontinence device of the invention.
Figure 16:
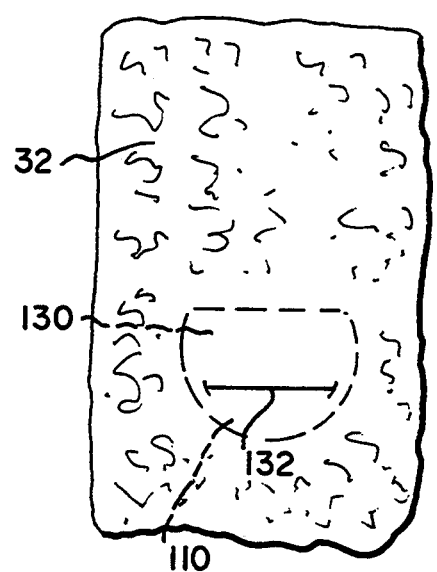
FIG. 16 is a plan view from the inside of a portion of the novel incontinence device of FIG. 15.

Referring now to FIG. 15 and 16 a modified flap 130 and a modified slit 132 are employed in brief 20. In this embodiment slit 132 is disposed transversely in brief 20 instead of longitudinally as heretofore described with respect to the other embodiments. The flap 130 is designed to cover the lower portion 110 of slit 132 and provide a permanent fluid tight seal from point 134 to point 136 to contain fluids in lower portion 110 between flap 130 and outer cover 28 of brief 20. A second reclosable seal 138 is provided in the portion above lower portion 110 with spot heat seals 140 and 142 which may be broken when the brief is used by the male to provide access and to expose the second reclosable seal 138.

Referring now to FIGS. 17-20 other arrangements and configurations for flap 50 are illustrated. In FIG. 17 a triangular shaped flap permanently sealed only at the bottom portion 150 is illustrated which does not cover the entire length of slit 44. The upper end of slit 44 remains open to improve aeration to the interior of the brief which may be further augmented by providing a means for spacing the flap away from cover 28 as has heretofore been described.

FIGS. 18, 19 and 20 illustrate additional configurations and arrangements for the flap 50 as well as further divisions between permanent seals 160 such as heat seal 54 and a reusable seal 162 such as second seal 60. The permanent seal can be from 0 to 100 percent of the perimeter of the flap. In the preferred application of the invention the permanent seal is from about 25 percent to 85 percent of the perimeter of the flap with the remaining portion of the seal being a reusable seal. A spot seal 164 may be provided at the corners to hold the flap in place before the flap is opened or if the flap is to remain closed. The spot seal can either be a permanent seal or a reclosable seal.

The combination of slit or semi perforated opening with the flap closure together with a seal provides a universal incontinence device that may be utilized by both the male and female. The novel incontinence device not only provides access for the male but also provides aeration to the interior of the garment to promote comfort and to prevent unnecessary discarding of the garment to add further bulk to landfill and damage to the environment.

As a result a novel universal incontinence device of the invention provides psychological as well as physiological advantages to the patient in not only providing for normal urination by male patients but also aeration and comfort in not having to remove and then try to replace garments for normal urination. In addition the invention provides advantages to the environment in allowing the garment not to be discarded when it is not soiled and provides a single garment which can be utilized for a multitude of functions thereby decreasing the number of packages and packaging as well as the great number and variety of incontinence devices which have heretofore unfortunately found their way into land fill or become a problem for disposal. The novel universal incontinence device of the invention is about the same bulk as other incontinence devices on the market and is little if at all more expensive to produce than prior art incontinence devices that are not universal.

The invention may be implemented in a variety of ways utilizing the slit or semi perforated opening together with the flap for providing a universal incontinence device for use by both males and females and providing access for the male to provide normal urination. The flap may be modified to include dyes or indicators to display a need to change the device for the severely incontinent or bedridden. The shape of the flap may be modified to any desired geometrical configuration. The flap may also be modified to provide additional aeration to the inside of the diaper to provide additional comfort in view of modern efforts to more completely seal the diaper at the legs, waist and other areas, particularly in view of the waterproof nature of the outer covering.

These advantages of aeration, comfort and environmental advantages by reducing the number and variety of incontinent devices as well as associated packaging required for the diversity of incontinence devices may be accomplished by utilizing the novel universal incontinence device. In addition the nature of the seal between the flap and the outer layer of the incontinence device may be changed or modified to suit particular requirements or modified to provide multiple seals within the scope and spirit of the invention as defined in the following claims:

What is claimed is:

1. An incontinence device comprising:
   (a) a front section having a liquid absorbent layer and a liquid resistant exterior surface;
   (b) a center section having an absorbent material for collecting body fluids, said center section communicating with said front section;
   (c) a rear section communicating with said center section;
   (d) a waist band for connecting said rear section to said front section;
   (e) a medial semi perforated opening extending through said liquid absorbent layer and said liquid resistant exterior surface of said front section, said medial semi perforated opening extending upwardly toward said waist band said medial semi perforated opening terminating below said waist band to provide an optional access from said exterior surface to the interior surface of said front section;
   (f) a liquid resistant flap cover for covering said medial semi perforated opening; and
   (g) a seal for sealing the entire perimeter of said liquid resistant flap cover to said liquid resistant exterior surface of said front section.

2. The incontinence device of claim 1 wherein said liquid resistant flap cover includes a liquid absorbent inner layer.

3. The incontinence device of claim 2 wherein said liquid resistant flap cover includes an indicator dye disposed between said liquid resistant flap cover and said liquid absorbent inner layer.

4. The incontinence device of claim 2 further comprising a pressure sensitive second seal protected by a removable protective layer.

5. The incontinence device of claim 1 further comprising a moisture pervious inner liner disposed in said front section and said center section.

6. The incontinence device of claim 5 wherein said medial semi perforated opening extends through said moisture pervious inner liner.

7. The incontinence device of claim 6 further comprising a second perforation at the ends of said medial semi perforated opening to prevent tearing.

8. The incontinence device of claim 5 wherein said waist band is an elasticized waist band.

9. A universal incontinence device comprising:
   (a) a front section having a liquid resistant exterior surface said front section terminating in a waist band area at the uppermost portion of said front section;
   (b) a center section for collecting body fluids having an absorbent material communicating with said front section said center section terminating in a rearward portion;
   (c) means for connecting said front section to said rearward portion of said center section;
   (d) a slit in said front section for providing access to the interior surface of said center section through said front section said slit extending upwardly toward said waist band area and terminating at a point below said waist band area;
   (e) a flap cover having a liquid resistant outer surface for covering the major portion of said slit said slit and said flap cooperating to provide optional access to the interior surface of said center section through said front section; and
   (f) a seal for sealing at least a portion of the perimeter of said flap cover to said liquid resistant exterior surface of said front section.

10. The universal incontinence device of claim 9 wherein said seal is a heat bonded seal connecting said liquid resistant outer surface of said flap cover with said liquid resistant exterior surface of said front section.

11. The universal incontinence device of claim 10 wherein the inner surface of said flap cover includes a moisture indicator dye.

12. The universal incontinence device of claim 11 further comprising a liquid absorbent layer covering said moisture indicator dye.

13. The universal incontinence device of claim 10 further comprising a pressure sensitive second seal protected by a removable protective layer.

14. The universal incontinence device of claim 10 wherein said flap cover includes an opening extending from the upper perimeter of said flap cover down to said slit.

15. The universal incontinence device of claim 14 wherein said opening is maintained by spacing said upper perimeter of said flap cover away from said liquid resistant exterior surface of said front section.

16. The universal incontinence device of claim 9 wherein said flap cover includes a perforation which is not in alignment with said slit.

17. In a moisture absorbent brief with a front section having a waist area and a liquid resistant outer surface and a center section for collecting body fluids and an absorbent material communicating between said front section and said center section and means for attaching said moisture absorbent brief to the body of a wearer wherein, the improvement comprising:
(a) a medial semi perforated opening communicating from the outer surface of said liquid resistant front section to the inside of said front section, said medial semi perforated opening terminating at a point below said waist area;
(b) a liquid resistant flap cover for covering said medial semi perforated opening; and
(c) a seal formed around the perimeter of said liquid resistant flap cover and said liquid resistant outer surface of said front section.

18. The moisture absorbent brief of claim 17 further comprising a moisture pervious inner liner disposed in said front section and said center section.

19. The moisture absorbent brief of claim 18 wherein said medial semi perforated opening extends through said moisture pervious inner liner.

20. The moisture absorbent brief of claim 19 further comprising a second perforation at the ends of said medial semi perforated opening to prevent tearing.

* * * * *